United States Patent
Brown et al.

(10) Patent No.: US 6,440,068 B1
(45) Date of Patent: Aug. 27, 2002

(54) MEASURING USER HEALTH AS MEASURED BY MULTIPLE DIVERSE HEALTH MEASUREMENT DEVICES UTILIZING A PERSONAL STORAGE DEVICE

(75) Inventors: Michael Wayne Brown, Georgetown; Kelvin Roderick Lawrence; Michael A. Paolini, both of Round Rock, all of TX (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/560,996

(22) Filed: Apr. 28, 2000

(51) Int. Cl.$^7$ .................................................. A61N 5/00
(52) U.S. Cl. .......................................... 600/300; 705/1
(58) Field of Search ................................ 600/300–301, 600/302, 303, 304, 305; 705/1–5

(56) References Cited

U.S. PATENT DOCUMENTS

| | | | |
|---|---|---|---|
| 5,410,471 A | | 4/1995 | Alyfuku et al. |
| 5,720,619 A | | 2/1998 | Fisslinger |
| 5,823,948 A | * | 10/1998 | Ross, Jr. et al. ............ 600/300 |
| 6,234,963 B1 | * | 5/2001 | Blike et al. ................. 600/300 |
| 6,248,067 B1 | * | 6/2001 | Causey, III et al. ........ 600/365 |
| 6,272,469 B1 | * | 8/2001 | Koritzinsky et al. ........... 705/2 |

OTHER PUBLICATIONS

The Wall Street Journal, Thomas E. Weber, Jan. 17, 2000 A Doctor, 700 Patients And The Net: Inventing The Virtual House Call.
iButton Overview, "What is an iButton?".
Johnson & Johnson, Lifescan, In Touch Diabetes Management Software, "Chart A Course to Better Blood Glucose Management" 1999.

* cited by examiner

Primary Examiner—Kevin Shaver
Assistant Examiner—Pamela Wingood
(74) Attorney, Agent, or Firm—Marilyn Smith Dawkins; Bracewell & Patterson, L.L.P.

(57) ABSTRACT

According to the present invention, physical health indicators computed for a particular user are received in a common transmittable data format at a computer system, wherein each of the physical health indicators is output by an electronic health measurement device from among multiple diverse electronic health measurement devices monitoring the physical health of the particular user. Each of the physical health indicators is analyzed at the computer system in view of acceptable health levels retrieved at the computer system from a personal storage device proffered by the particular user. Output of an indicator of acceptability of the physical health indicators for the particular user is controlled from the computer system, in response to the analysis of each of the physical health indicators, such that a computer system monitors the physical health of an individual in view of acceptable health levels retrieved from the personal storage device.

26 Claims, 7 Drawing Sheets

| UCID | Password | Birthdate | Heart Rate Range/ Exercise | Heart Rate Range/ Resting | Respiration Rate/ Exercise | Respiration Rate/ Resting | |
|---|---|---|---|---|---|---|---|
| GeorgeG | 45ghr5 | 10.20.1945 | 60-120 | 60-80 | 20-25 | 15-18 | ... |
| SylviaS | Cats20 | 06.06.1948 | 70-130 | 60-75 | 22-26 | 16-20 | ... |
| ... | ... | ... | ... | ... | ... | ... | ... |

Fig. 5

MEASURING USER HEALTH AS MEASURED BY MULTIPLE DIVERSE HEALTH MEASUREMENT DEVICES UTILIZING A PERSONAL STORAGE DEVICE

BACKGROUND OF THE INVENTION

1. Technical Field

The present invention relates in general to a health monitoring device and in particular to a method, system and program for monitoring the outputs of multiple diverse health measurement devices. Still more particularly, the present invention relates to a method, system and program for monitoring physical health indicators received from multiple diverse health measurement devices at a single personal storage device and managing multiple diverse health control devices according to normal physical health levels for a user retrieved from the personal storage device.

2. Description of the Related Art

Conventional electronic health measurement devices provide for taking measurements that are computed to reflect the physical health of an individual. In particular, an electronic health measurement device is able to translate a measurement, such as weight on a scale, into a numerical output. For example, diabetics utilize electronic testers that monitor blood or other secretions to determine a number associated with the individual's current glucose levels. In another example, an electronic pulse detector may be placed on an individual's body or gripped by the individual in order to detect the user's current pulse level and compute a numerical representation of the pulse level. In these examples, the computed numbers are associated with a scale of measurement that has been assigned to that type of physical health measurement. An individual may be able to consult a chart or other documentation to discern the meaning of the computed number. For example, a computed weight may be compared with a chart containing preferable weights for an individual of a particular height and age. A computed pulse level may be compared with a chart showing acceptable pulse levels during exercise depending upon age.

While conventional electronic health measurement devices provide a computed number that can be utilized by an individual to monitor that portion of their physical health, there is a need for electronically documenting the measured data in a timely manner. In addition, while some electronic health measurement devices do provide for electronically documenting the measured data, there is a need to electronically document output data from multiple diverse electronic health measurement devices at a single device such that a comprehensive physical health profile can be determined. Moreover, while an individual may be able to consult a chart or other textual data to discern the meaning of a number computed by an electronic health measurement device, this data is not always available, may not be current, may not provide recommendations for how to respond to particular measurement values, and may not provide analysis of measurements from multiple diverse electronic health measurement devices.

In view of the foregoing, it is desirable that a method, system and program be provided for storing monitored health related data retrieved from diverse electronic health measurement devices at a single personal storage device and managing multiple diverse health control devices according to normal physical health levels for a user retrieved from the personal storage device.

SUMMARY OF THE INVENTION

In view of the foregoing, it is therefore an object of the present invention to provide an improved health measurement monitoring device.

It is another object of the present invention to provide an improved method, system and program for the output of monitoring multiple diverse health measurement devices.

It is yet another object of the present invention to provide an improved method, system and program for monitoring physical health indicators received from multiple diverse health measurement devices at a single personal storage device and managing multiple diverse health control devices according to normal physical health levels for a user retrieved from the personal storage device.

According to the present invention, physical health indicators computed for a particular user are received in a common transmittable data format at a computer system, wherein each of the physical health indicators is output by an electronic health measurement device from among multiple diverse electronic health measurement devices monitoring the physical health of the particular user. Each of the physical health indicators is analyzed at the computer system in view of acceptable health levels retrieved at the computer system from a personal storage device proffered by the particular user. Output of an indicator of acceptability of the physical health indicators for the particular user is controlled from the computer system, in response to the analysis of each of the physical health indicators, such that a computer system monitors the physical health of an individual in view of acceptable health levels retrieved from the personal storage device.

All objects, features, and advantages of the present invention will become apparent in the following detailed written description.

BRIEF DESCRIPTION OF THE DRAWINGS

The novel features believed characteristic of the invention are set forth in the appended claims. The invention itself, however, as well as a preferred mode of use, further objects, and advantages thereof, will best be understood by reference to the following detailed description of an illustrative embodiment when read in conjunction with the accompanying drawings, wherein:

FIG. 5 depicts one embodiment of a block diagram of a data storage structure for health profiles in accordance with the method, system and program of the present embodiment;

DETAILED DESCRIPTION OF ILLUSTRATIVE EMBODIMENT

The present invention may be executed in a variety of systems, including a variety of computer systems under a number of different operating systems where the system has access to a personal storage device. In a preferred embodiment of the present invention, the computer system is a desktop computer, a network computer, a midrange computer or a mainframe computer. However, in alternate embodiments, the computer system may also be a portable computing system such as a laptop computer, a personal digital assistant, or cellular telephone. In addition, the computer system may be a stand-alone system or part of a network such as a local-area network (LAN) or a wide-area network (WAN). The personal storage device may be a smart card, an ibutton™ microprocessor (ibutton is a trademark of Dallas Semiconductors, Inc.), or other portable storage device that stores data for a particular user or users and is easily transportable. Therefore, in general, the present invention is preferably executed on a computer system that performs computing tasks such as manipulating data from a personal storage device that is accessible to the computer system.

Figure 1:
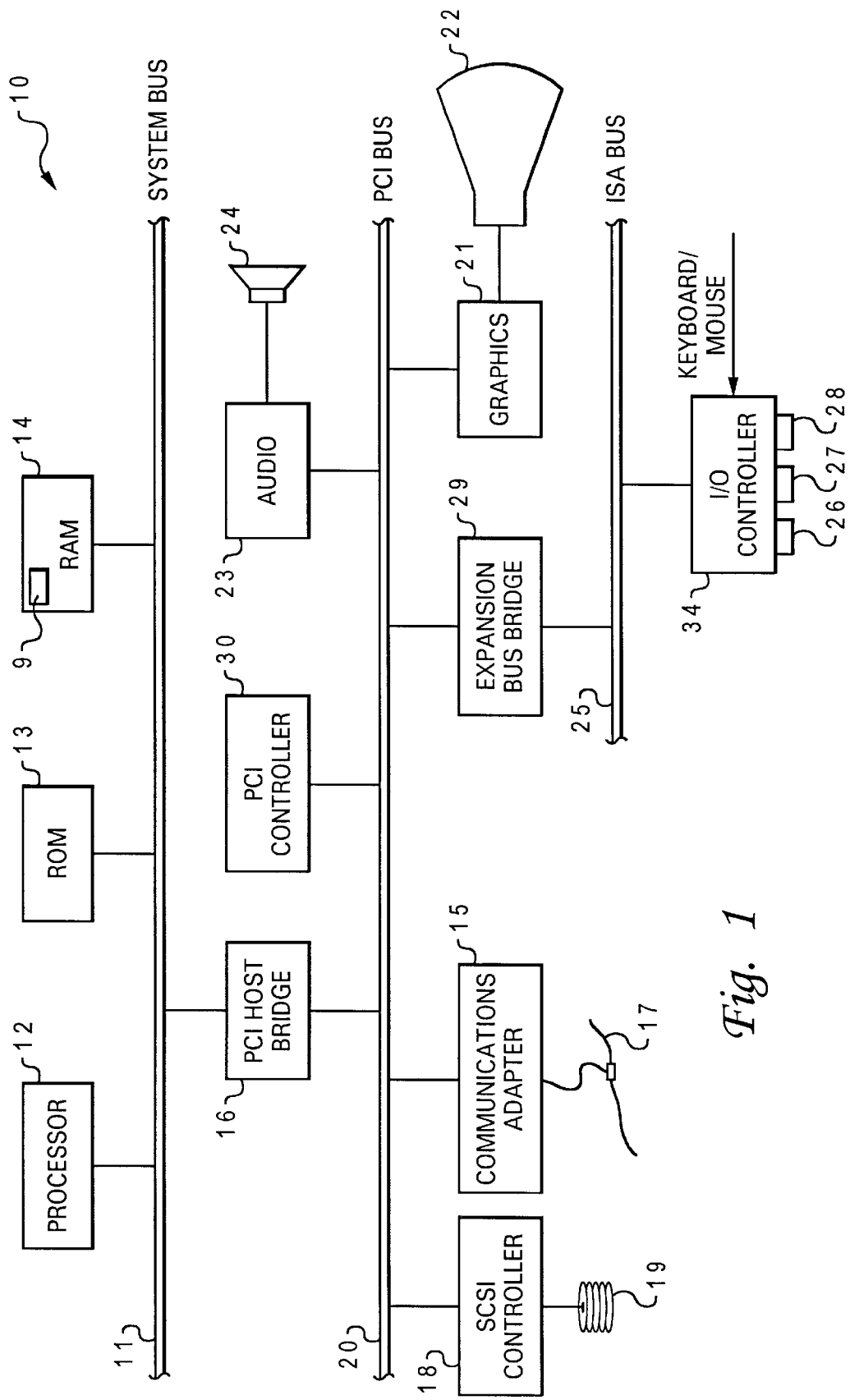
FIG. 1 depicts one embodiment of a data processing system with which the method, system and program of the present invention may advantageously be utilized.

Referring now to the drawings and in particular to FIG. 1, there is depicted a block diagram of one embodiment of a computer system that may utilize the present invention. As depicted, data processing system 10 includes at least one processor 12, which is coupled to system bus 11. Each processor 12 is a general-purpose processor, such as IBM's PowerPC™ processor that, during normal operation, processes data under the control of operating system and application software stored in random access memory (RAM) 14 and Read Only Memory (ROM) 13. The operating system preferably provides a graphical user interface (GUI) to the user. Application software contains instructions that when executed on processor 12 carry out the operations depicted in the flowcharts of FIGS. 6, 7, 8, and others described herein.

Processors 12 are coupled via system bus 11 and Peripheral Component Interconnect (PCI) host bridge 16 to PCI local bus 20. PCI host bridge 16 provides a low latency path through which processor 12 may directly access PCI devices mapped anywhere within bus memory and/or I/O address spaces. PCI host bridge 16 also provides a high bandwidth path for allowing PCI devices to directly access RAM 14.

PCI local bus 20 interconnects a number of devices id for communication under the control of PCI controller 30. These devices include a Small Computer System Interface (SCSI) controller 18, which provides an interface to SCSI hard disk 19, and communications adapter(s) 15, which interface data processing system 10 to at least one data communication network 17 comprising wired and/or wireless network communications. In addition, an audio adapter 23 is attached to PCI local bus 20 for controlling audio output through speaker 24. A graphics adapter 21 is also attached to PCI local bus 20 for controlling visual output through display monitor 22. In alternate embodiments of the present invention, additional peripheral components may be added. For example, in alternate embodiments, a tactile display component may be provided.

PCI local bus 20 is further coupled to an Industry Standard Architecture (ISA) bus 25 by an expansion bus bridge 29. As shown, ISA bus 25 has an attached I/O (Input/Output) controller 34 that interfaces data processing system 10 to peripheral input devices such as a keyboard and mouse (not illustrated) and supports external communication via parallel, serial and universal serial bus (USB) ports 26, 27, and 28, respectively.

Figure 2:
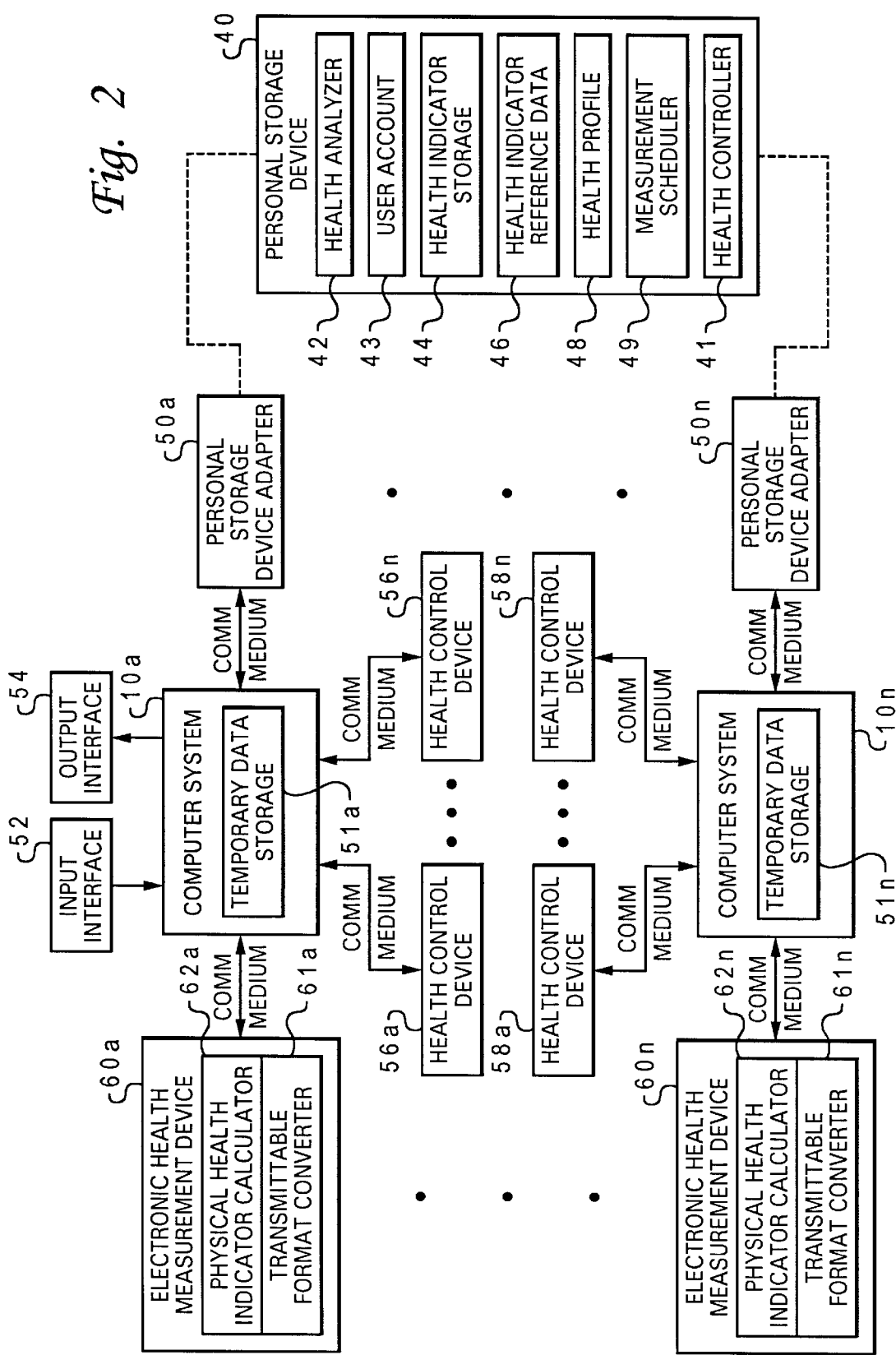
FIG. 2 illustrates one embodiment of a block diagram of an electronic health measurement device monitoring system in accordance with the method, system and program of the present invention.

With reference now to FIG. 2, there is illustrated a block diagram of an electronic health measurement device monitoring system in accordance with the method, system and program of the present invention. As depicted, computer systems 10a–10n communicate with multiple diverse electronic health measurement devices 60a–60n via a communications medium (or across a communications interface). In addition, computer systems 10a–10n communicate with personal storage adapter devices 50a–50n via a communications medium. Moreover, computer systems 10a–10n communicate with health control devices 56a–56n and 58a–58n via communications mediums.

The communications medium may include wired or wireless communications or other communications media that enables transmission of data. Moreover, the communications medium may include a network, such as the Internet, or a straight data link. In a wired embodiment of the communications medium, for example, electronic health measurement devices 60a–60n and adapter devices 50a–50n are connected to computer systems 10a–10n via parallel, serial, USB ports or the network connection as depicted in FIG. 1. In a wireless embodiment of the communications medium, for example, electronic health measurement devices 60a–60n and adapter devices 50a–50n are connected to computer systems 10a–10n via infrared, radio frequency (RF), cellular and other wireless transmissions which are detected by computer systems 10a–10n.

Data exchange across the communications medium is advantageously performed in at least one of multiple available data transmission protocols and is preferably supported by a common data structure format, such as the extensible mark-up language (XML) data format. Data transmission protocols may include, but are not limited to, Transmission Control Protocol (TCP), Internet Protocol (IP), Hypertext Transfer Protocol (HTTP), and Bluetooth. In addition, data may be transmitted in a secure manner via encryption or by technologies, such as secure socket layer (SSL) or virtual private networks (VPN).

An example of an XML data file that might be transmitted from electronic health measurement devices 60a–60n to computer systems 10a–10n, as depicted below, preferably contains data that is distinguished by attributes on elements and may be wrappered within a larger element. For example, the data attributed to element "<TimeStamp> </TimeStamp>" designates the time that the data was attributed to the XML data file.

<PULSE TimeStamp="888965153" TimeRange="888965153, 888965185" MachineType="Pulse345" Rate="80">

In addition, in an alternate example, the XML data file might be formatted utilizing elements, as illustrated below.

<TimeStamp>888965153</TimeStamp>
<TimeRange>888965153,888965185</TimeRange>
<MachineType>Pulse345</MachineType>
<Rate>80</Rate>

In the example, as will be further described, computer systems 10a–10n would receive the example XML data file and utilize the XML data file to compare with a suitable pulse level for a user. The above described XML data file example is intended as a functional example of an XML data file that would detail the pulse rate of an individual. The elements, format of the elements and data included with the elements is provided to depict an example and is not intended to limit the types of elements, format of elements or data included with elements that are in an XML data file.

In the example of the XML data format as the common transmittable data format, a data validation file such as a document type definition (DTD) or schema is preferably utilized to validate XML data files. In addition, a schema preferably translates multiple XML data files. Moreover, a style sheet such as an extensible stylesheet language (XSL) file is preferably utilized to provide a style specification for the XML data at the receiving system. In particular, DTDs, schemas, and XSL files may be, for example, transmitted with an XML data file to a receiving system or downloaded at the receiving system from an alternate source. In the present example, the DTD or schema would verify that all the data required for reading a pulse is included in the XML data file.

Health measurement devices 60a–60n preferably include multiple diverse health measurement devices, such as a pulse monitor, a blood pressure monitor, an electronic secretion monitor, a perspiration monitor, an electronic scale, an electronic body fat monitor, a stress monitor, a carpal movement monitor, a distance monitor, a respiration monitor, a glucometer, and monitoring devices that monitor at least one aspect of a user's health. Each of health measurement devices 60a–60n preferably includes a physical health indicator calculator 62a–62n. Physical health indicator calculators 62a–62n preferably compute a numerical physical health indicator of physical health data measured by health measurement devices 60a–60n for a user. In particular, in computing numerical physical health indicators, the computed numbers are preferably associated with a scale of measurement that has been assigned to that type of physical health measurement. Physical health indicators computed by physical health indicator calculators 62a–62n are preferably converted into a common transmittable data format by transmittable format converters 61a–61n, such as XML, and transmitted via the communications medium to computer systems 10a–10n.

Computer systems 10a–10n preferably include, but are not limited to including, temporary data storage 51a–51n, such as RAM or cache. Personal storage device adapters 50a–50n preferably reads from and writes to a personal storage device 40. Personal storage device 40 preferably includes, but is not limited to including, a data storage medium, an encryption medium and a processor. The data storage medium of personal storage device 40 preferably includes, but is not limited to including, a health controller 41, a health indicator analyzer application 42, a user account 43, a health indicator storage 44, a health indicator reference 46, a health profile 48, and a measurement scheduler 49. Data and applications stored in personal storage device 40 are preferably uploaded to temporary data storage 51a–51n when personal storage device 40 is proffered from a user.

In particular, health controller 41, health indicator analyzer 42 and measurement scheduler 49 are preferably applications that are transmitted to temporary data storage 51a–51n and executed on computer systems 10a–10n. For example, the applications may be java applets executable on computer systems 10a–10n. Alternatively, for a personal storage device 40 with substantial processing power, the applications may be executed on personal storage device 40, such that computer systems 10a–10n are utilized as "dumb" terminals. Moreover, in an alternate embodiment of the invention, computer systems 10a–10n may further include health related applications, such as a health indicator analyzer application. Furthermore, additional applications may be stored on personal storage device 40 and uploaded to temporary data storage 51a–51n to control additional monitoring functions.

Therefore, computer system 10a may receive a personal storage device temporarily proffered by a user via personal storage device adapter 50a, receive monitored physical health indicators for the user from electronic health measurement device 60a, and transmit the monitored physical health indicator for storage at personal storage device 40. Over a period of time, a user may temporarily proffer personal storage device 40 at multiple computer systems 10a–10n in order to receive multiple diverse physical health indicator measurements. In addition, the user may receive adjustment to physical health from health control devices 56a–56n and 58a–58n.

Physical health indicators transmitted from health measurement devices 60a–60n to computer systems 10a–10n are preferably automatically stored in health indicator storage 44 of personal storage device 40. Health indicator storage 44 preferably utilizes a data storage structure for storing physical health indicators according to, for example, date and time taken and the type of health measurement device received. Each physical health indicator received at computer systems 10a–10n is preferably analyzed by health indicator analyzer 42 to provide the user with an analysis of the most recently received health indicator. In addition, health indicator analyzer 42 is preferably enabled to perform a variety of analysis including, but not limited to, a comprehensive overview of physical health according to all the physical health indicators stored on personal storage device 40, an overview of physical health according to physical health indicators received over a particular period of time on personal storage device 40, and an overview of physical health according to the health measurement device utilized.

Health indicator analyzer 42 is preferably enabled to analyze the physical health indicators stored for a user in health indicator storage 44 over a period of time in order to determine normal levels for a user when sleeping, eating, exercising and working. For example, if when eating over a span of ten days a user's heart rate is detected between 65 and 75 beats per minute, health indicator analyzer 42 may determine that a normal heart rate for the user when eating is between 65 and 75 beats per minute. Moreover, health indicator analyzer 42 is preferably enabled to analyze the physical health indicators over a period of time in order to determine moods associated with levels of physical health. For example, a mood of "happiness" may be associated with a particular pulse rate while a mood of "anxiety" may be associated with a particular level of perspiration for a particular user.

In addition to receiving physical health indicators from health measurement devices 60a–60n, a user may input physical health indicators into computer systems 10a–10n via an input interface, such as input interface 52 which may include, but is not limited to, a keyboard, a mouse, a stylus, and a vocal recognition system. Physical health indicators received from the input interface are preferably automatically stored in health indicator storage 44 of personal storage device 40. For example, a user may take his/her own pulse and enter the pulse rate into computer systems 10a–10n via an input interface rather than utilizing a health measurement device that computes a pulse rate. In addition, a user may input physical health indicators into computer system 10 via an input interface that are computed by a health measurement device that is not enabled to transmit physical health indicators.

Health profile 48 includes other health related and non-health related data stored for a user in personal storage device 40. For example, the user's birthdate, height, physical disabilities, injuries, doctors' information, and other relevant data may be provided. In addition, a range of acceptable health indicator levels for multiple types of physical health indicators may be included. Health indicator analyzer 42 may utilize data such as age, in analyzing physical health indicators. In addition, in analyzing physical health indicators, health indicator analyzer 42 may prompt a user to enter data for storage in health profile 48 that is relevant for the analysis. Moreover, health profile 48 may include security filters designating multiple levels of security for data stored on personal storage device 40. For example, the user may indicate that certain parts of health profile 48, such as the user's physical disabilities are to be shielded from transmittal and access unless a password is supplied. In another example, the user may indicate that only certain types of indicator measurements are transmittable to and/or accessible by a healthcare provider. As will be understood by one with ordinary skill in the art, multiple types of security methods and filters may be applied to the data, such as health indicator storage 44 and health profile 48, stored on personal storage device 40.

Health indicator reference 46 preferably includes reference data for each of the types of physical health indicators measured by health measurement devices 60a–60n, including recommended health indicator levels, instructions for compensating for levels and/or dealing with emergencies, and additional data which can be output to the user as needed. Data within health indicator reference 46 can preferably be accessed by the user at computer systems 10a–10n according to, for example, the health measurement device or type of physical health indicator. In addition, health indicator analyzer 42 may utilize data provided in health indicator reference database 46 in analysis and may include or point to data in health indicator reference database 46 in analysis reports provided to the user. Data stored within health indicator reference database 46 may be downloaded and updated.

In addition, in analyzing physical health indicators received at computer systems 10a–10n, other health related data for the user retrieved from personal storage device 40 may be utilized by health indicator analyzer 42 in analyzing the physical health indicators such as food, liquid and medication intake by the user over a period of time, fitness activity calculated for the user over a period of time, environmental exposure of the user over a period of time, and additional factors that may influence the health of an individual.

Results of analysis performed by health indicator analyzer 42 are preferably output to the user via an output interface, such as output interface 54, according to output preferences set by the user in health profile 48 of personal storage device 40. The user-designated output preferences may designate output to multiple types of peripherals accessible to computer systems 10a–10n. Examples of peripherals include, but are not limited to, a graphical display, an electronic paper, an audio speaker, audio headphones, a tactile detectable device, or a printer. In particular, the user may select and provide the type of output device and may upgrade the type of output device as technology advances. The output preferences may include, but are not limited to specifications such as the size, type and coloring of a font in a graphical display, the type of tactile-detectable output (e.g. Braille), the language or the metric amount displayed.

For a graphical display, the user can preferably select from and switch between multiple types of data presentations. For example, the user may select to view of chart or graph of the analyzed data. Alternatively, the user may select to view a spreadsheet representation of the analysis. As previously described, presentation of the data may include data from health indicator reference 46 or may provide a selectable link to particular data within health indicator reference 46. Additional types of data presentations which are not described here may also be utilized for displaying the analyzed data from health indicator analyzer 42.

In response to analysis performed by health indicator analyzer 42 in view of a range of acceptable health indicator levels for the user, instructions, recommendations and warnings may be output to the user or a warning signal may be triggered such that the user's condition will be dealt with. For example, if an acceptable heart rate for the user when exercising is determined as 120 beats per minute and the detected heart rate for the user while exercising is 150 beats per minute, a warning is preferably output to the user to reduce his/her level of exercise. In addition, recommendations such as increasing water consumption, particular stretches and additional information that would aid the user in lowering his/her heart rate may be provided, as retrieved from health indicator reference database 46.

In another example, computer systems 10a–10n for a user in a hospital may have access to a warning light or bell, such that in response to analysis of current physical health indicators for the user and analysis of the current physical health indicators in view of acceptable levels for the patient, a warning light or bell may be activated if the physical health indicators are outside of acceptable levels for the patient.

In addition, in response to analysis performed by health indicator analyzer 42, a control signal determined TA by health controller 51 may be output to health control devices 56a–56n via computer system 10a and to health control devices 58a–58n via computer system 10n. The control signal determined by health controller 51 requests adjustment to the user's health as controlled by those devices. Health control devices 56a–56n preferably include multiple diverse health control devices that each control a physical aspect of a user's bodily health. For example, in response to a blood sugar level measurement by a health measurement device, health indicator analyzer 42 may determine that the blood sugar level of the user is too low according to the user's health profile and/or the health indicator reference 46. Health controller 51 would determine a control signal to a health control device that injects glucose into the user at a controlled rate or reduces injection of insulin in order to increase the user's blood sugar levels to request adjustment to the user's health as controlled by those devices.

Moreover, computer system 10 may receive health profile 48 from personal storage device 40 and transmit a range of acceptable health indicator levels for the user from computer system 10 to health control devices 56a–56n. Health control devices 56a–56n advantageously utilize the acceptable health indicator levels to control output from the health control devices to the user. For example, acceptable health indicator levels transmitted to a computer system that is coupled to a bath water temperature controller may indicate that the water temperature must remain between 100° F. and 101° F. The bath water temperature controller would adjust the water temperature in order to maintain the range of acceptable water temperatures.

Measurement scheduler 49 provides control of preset scheduling of when particular types of measurements need to be taken, when the measurements need to be taken and controls whether or not the computer system is to automatically transmit the measurements to a particular server or data storage medium. As described for health indicator analyzer 42, measurement scheduler 49 is preferably an application that is transmittable to temporary data storage 42a–42n and is executable on computer systems 10a–10n. In an alternate embodiment, measurement scheduler may be executed on personal storage device 40 or may be stored on computer systems 10a–10n and executed therein.

Scheduling data may be entered via an input interface to a computer system by a user or from a health care professional or downloaded to the computer system and stored in a data storage structure associated with measurement scheduler 49. For example, a healthcare professional may designate that a user needs to take a blood glucose measurement every eight hours with the first measurement of the day occurring at 8 AM. Measurement scheduler 49 preferably stores indicators that blood glucose level measurement needs to be received at 8 AM, 4 PM and 12 AM. In addition, the health care professional may indicate the grace period for receiving the blood glucose level measurement for 2 hours. Therefore, receiving measurements between 7–9 AM, 3–5 PM and 11–1 AM is acceptable.

For each scheduled measurement, measurement scheduler 49 preferably provides a reminder or series of reminders to the user. For example, a user may be reminded at 7 AM that a measurement needs to be taken. If a measurement has not been received by 9 AM, the user may be reminded that the grace period for taking a measurement has expired. Measurement scheduler 49 may also include a calendar type of schedule to the user of when and what measurements need to be taken each day. In particular, if a measurement is not received at all, or is delayed, a record of the lack of receipt or delay may be added to health indicator storage 44. A healthcare professional may access health indicator storage 44 in order to view the measurements taken for a user and to monitor the timeliness of the user in taking measurements.

User account 43 preferably includes a user's account information, such as, but not limited to, a pre-paid balance, a credit card number, or checking number. In one embodiment of the present invention, for each use of health measurement devices 60a–60n detected at computer systems 10a–10n, the user is charged at user account 43. For example, a user may go to a clinic to utilize a selection of health measurement devices 60a–60n. For each usage, a pre-paid balance on user account 43 is decremented. Alternatively, for each usage, a billing amount is stored in user account 43 and automatically paid via credit before the user leaves. As previously described, multiple levels of security filters may be applied to user account 43 to limit transmittal and access to the data stored therein.

Personal storage device 40 is advantageously a smart card, a Java™-enabled ibutton microprocessor (Java™ is a trademark of Sun Microsystems, Inc.) or other personal storage device that is easily transportable. In addition, personal storage device 40 is customizable to a user's preferences and storage/encryption needs. For example, a user may select a personal storage device with a large storage medium or a small storage medium. Moreover, personal storage device 40 may include additional applications, such as java applets that are transmitted to computer system 10 and executed therein or are executed on personal storage device 40. Such applications may provide, for example, a user interface for entering data to be stored in health profile 48.

It is important to note that personal storage device adapter 38 may be enabled to read from and write to multiple types of personal storage devices, or only a single type of personal storage device. For example, a smart card reader/writer reads from and writes to smart cards. In another example, an ibutton receptor reads from and writes to a java ring or other ibutton based personal storage device. However, a reader/writer may combine both functions of the smart card reader/writer and the ibutton receptor. In addition, advantageously, personal storage device readers/writer can detect and transmit wireless transmissions, such as an RF transmissions, with the personal storage device. In addition, personal storage device readers/writers can detect and transmit data transmissions through contact with the personal storage device.

Moreover, it is important to note that personal storage device 40 is preferably proffered by a user by multiple personal storage device adapters that have access to multiple computer systems, such that physical health indicators can be retrieved and stored on personal storage device 40 from multiple types of computer systems that monitor multiple types of health measurement devices. In addition, it is important to note that a single personal storage device adapter may access multiple personal storage devices and in particular multiple health profiles from multiple personal storage devices, wherein applications executing on computer system 10 may utilize the multiple health profiles in analyzing physical health indicators and determining control signals for transmittal to available health control devices.

Furthermore, personal storage device 40 may be proffered by a particular user with a health profile stored on personal storage device 40 for that particular user. Alternatively, in the case of a machine, animal, or other object, personal storage device 40 may be proffered by a particular user on behalf of the machine, animal, or other object with a health profile stored on the personal storage device for that machine, animal or other object.

In addition, it is important to note that computer systems 10a–10n may represent multiple diverse computer systems that monitor data in addition to physical health indicators. For example, a computer system from among computer systems 10a–10n may monitor exercise performed by a user at an exercise machine. Therefore, a heart rate that is normal for the user while exercising is retrieved from personal storage device 40 and compared with a heart rate monitored at the computer system. In another example, a computer system may include a computer utilized by the user at work. A carpal movement monitor may monitor keystrokes or mouse strokes by the user and transmit the monitored data to the computer system. The user's carpal movement maximum is retrieved from personal storage device 40 at the computer and compared with the monitored strokes. The computer may provide warnings to the user as the user approaches the maximum and may even shutdown the computer after the maximum is exceeded by a particular amount.

Figure 3:
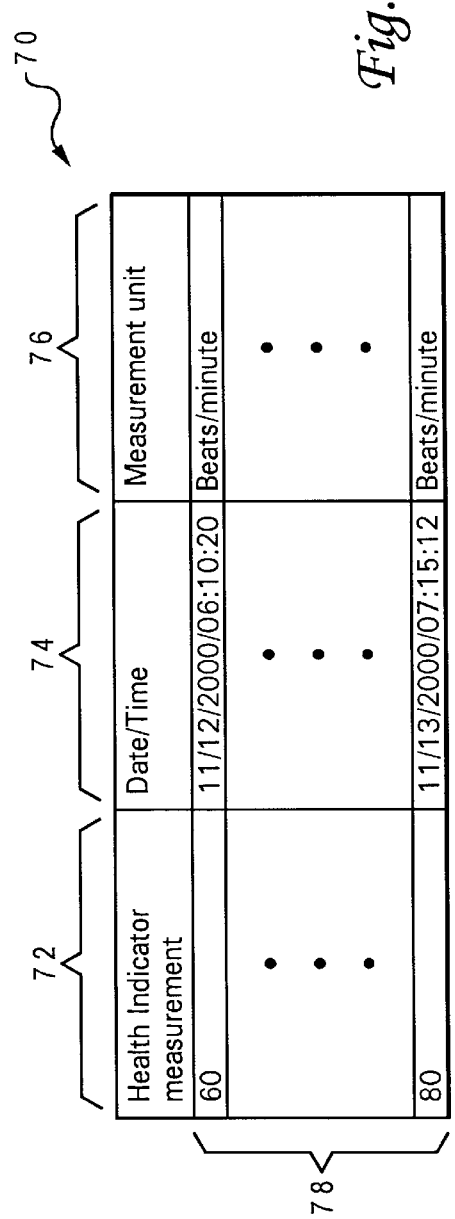
FIG. 3 depicts one embodiment of a block diagram of a data storage structure for the health indicator storage in accordance with the method, system and program of the present invention.

Referring now to FIG. 3, there is depicted a block diagram of a data storage structure for the health indicator storage in accordance with the method, system and program of the present invention. As depicted, a data storage structure 70 includes multiple categorized entries. Health indicators and other data from multiple types of health measurement devices may be stored in data storage structure 70 as converted from an XML data file, for example. While one type of data storage structure is depicted, in alternate embodiments, alternate types of data storage structures may be utilized. In addition, the user for which health indicators have been received is preferably designated in data storage structure 80 when there are multiple users A first category indicated at reference numeral 72 includes health indicator measurements. Next, a second category indicated at reference numeral 74 designates the date and time that the indicator measurement was taken. Thereafter, a third category indicated at reference numeral 76 includes the measurement unit. In the example provided, multiple entries are provided in each category as depicted at reference numeral 78. For example, on "Nov. 20, 2000" at "06:10:20" a pulse rate measurement taken in beats/minute was recorded with 60 beats/minute.

Figure 4:
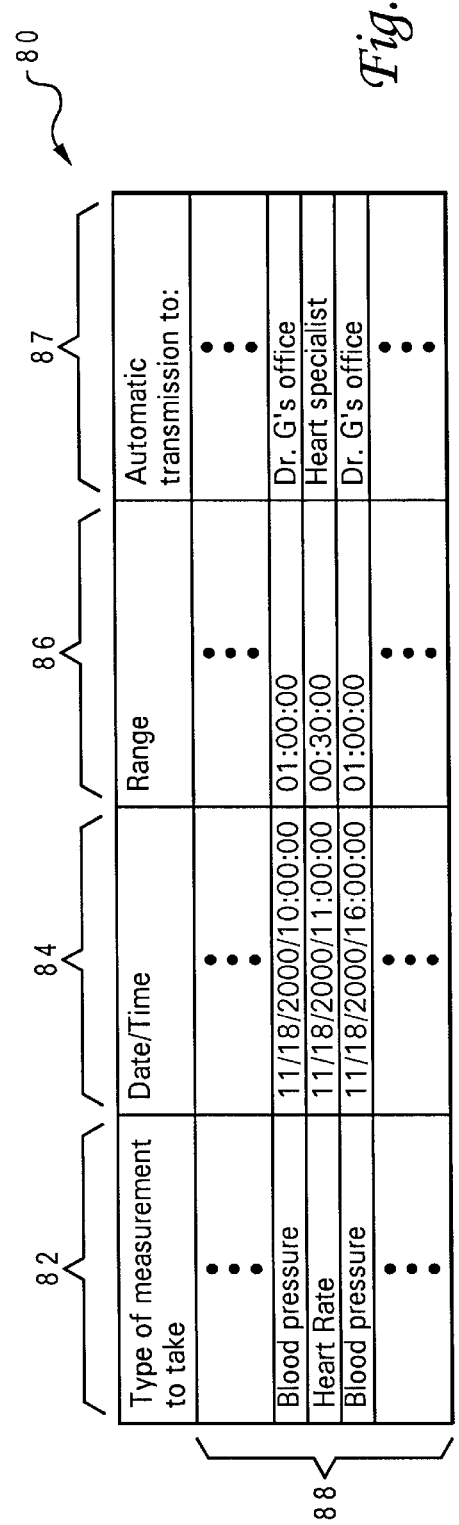
FIG. 4 illustrates one embodiment of a block diagram of a data storage structure for the measurement scheduler in accordance with the method, system and program of the present invention.

With reference now to FIG. 4, there is illustrated a block diagram of a data storage structure for the measurement scheduler in accordance with the method, system and program of the present invention. As depicted, a data storage structure 80 includes multiple categorized entries. Measurement scheduling for multiple types of health measurement devices may be stored in data storage structure 80. While one type of data storage structure is illustrated, in alternate embodiments, alternate types of data storage structures may be utilized. In addition, the user for which measurements have been scheduled is preferably designated in data storage structure 80 when there are multiple users.

A first category indicated at reference numeral 82 includes the type of measurement to take. Next, a second category indicated at reference numeral 84 designates the date and time to take the measurement. Thereafter, a third category indicated at reference numeral 86 includes the range of time. A fourth category indicated at reference numeral 87 designates where an automatic transmission of the measurement should be routed. In the example provided, multiple entries are provided in each category as depicted at reference numeral 88. For example, blood pressure readings are scheduled to be taken on "Nov. 18, 2000" between "9:00:00" and "11:00:00" and between "15:00:00" and "17:00:00". In addition, in the example, a heart rate reading is scheduled to be taken on "Nov. 18, 2000" between "10:30:00" and "11:30:00". The blood pressure readings are to be automatically transmitted to "Dr.G's office" and the heart rate transmitted to the "Heart Specialist". Advantageously, a server location other data storage system is associated with the tags depicted.

Referring now to FIG. 5, there is depicted a block diagram of a data storage structure for health profiles in accordance with the method, system and program of the present embodiment. As illustrated a data storage structure 90 includes multiple categorized entries. Health profiles for multiple users may be stored in data storage structure 90. While one type of data storage structure is illustrated, in alternate embodiments, alternate types of data storage structures may be utilized.

A first category indicated at reference numeral 91 includes the userID. Next, a second category indicated at reference numeral 92 designates the password for the userID. Thereafter, a third category indicated at reference numeral 93 includes the birth date. Next, a fourth category indicated at reference numeral 94 designates a heart rate range for the user while exercising. Thereafter, a fifth category indicated at reference numeral 95 includes a heart rate range for the user while resting. Next, a sixth category indicated at reference numeral 96 designates a respiration rate for the user while exercising. Thereafter, a seventh category indicated at reference numeral 97 includes a respiration rate for the user while resting.

In the examples provided, multiple entries are provided in each category as depicted at reference numeral 99. For example, a user "GeorgeG" has a password of "45ghr5" and was born on "Oct. 20, 1945". In addition, normal ranges of heart rates while exercising and resting are included respectively as 60–120 beats per minute (bpm) and 60–80 bpm. Moreover, the normal ranges or respiration rates while exercising and resting are includes respectively as 20–25 breaths per minute and 15–18 breaths per minute.

The user profile data stored in data storage structure 90 is preferably easily convertable into an XML data file. For example, the following is an example of an XML data file that may be converted from data storage structure 90.

<UserID>GeorgeG</UserID>
<Age>50</Age>
<Weight>190</Weight>
<HRExercise>60,120</HRExercise>
<HRResting>60,80</HRResting>
<RRExercise>20,25</RRExercise>
<RRResting>15,18<RRResting>

Figure 6:
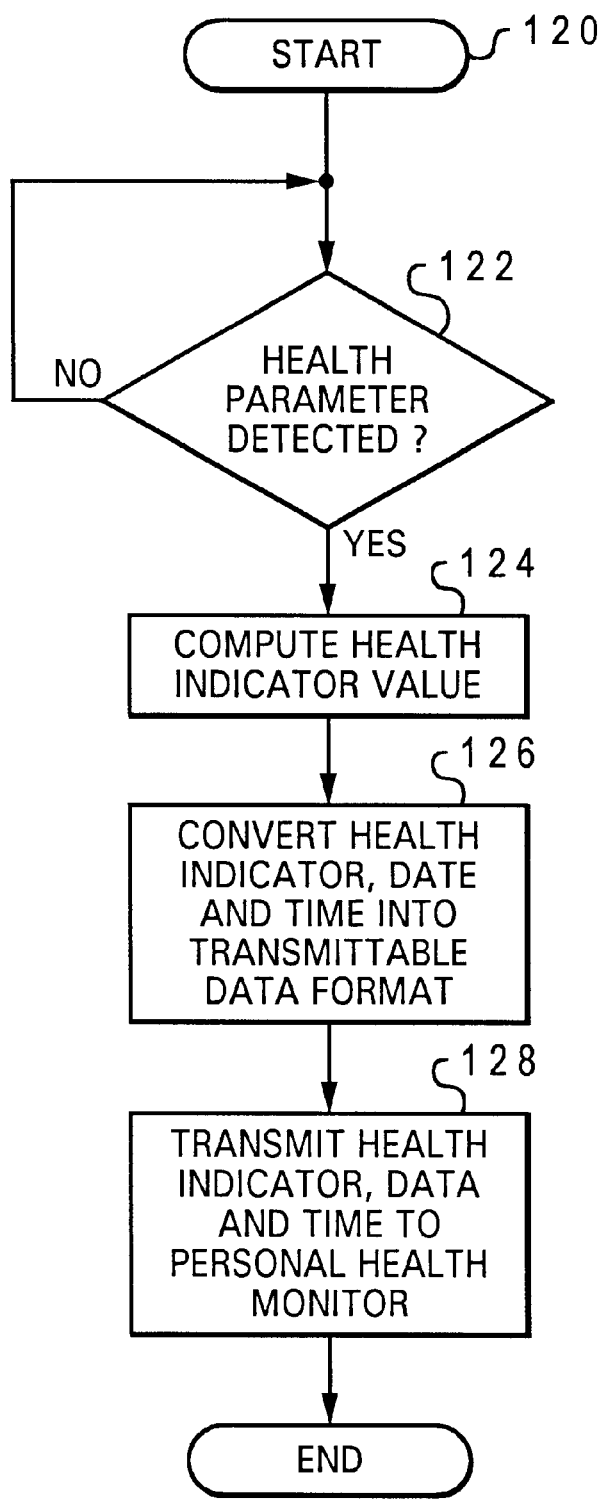
FIG. 6 illustrates a high level logic flowchart of a process and program for transmitting health indicators to a personal health indicator monitoring system in accordance with the method, system and program of the present invention.

With reference now to FIG. 6, there is illustrated a high level logic flowchart of a process and program for transmitting health indicators to a personal health indicator monitoring system in accordance with the method, system and program of the present invention. As depicted, the process starts at block 120 and thereafter proceeds to block 122. Block 122 illustrates a determination as to whether or not a health parameter is detected. Each health measurement device will detect different types of health parameters. For example, a pulse measurement device will detect a pulse rate for a user. If a health parameter is not detected, the process iterates at block 122. If a health parameter is detected, the process passes to block 124. Block 124 depicts computing a health indicator value. In the example of the pulse measurement device, a health indicator value of beats/minute is preferably computed. Thereafter, block 126 illustrates converting the health indicator and date and time of receipt into a common transmittable data format. Next, block 128 depicts transmitting the health indicator and data and time of receipt to a personal health monitor and the process ends.

Figure 7:
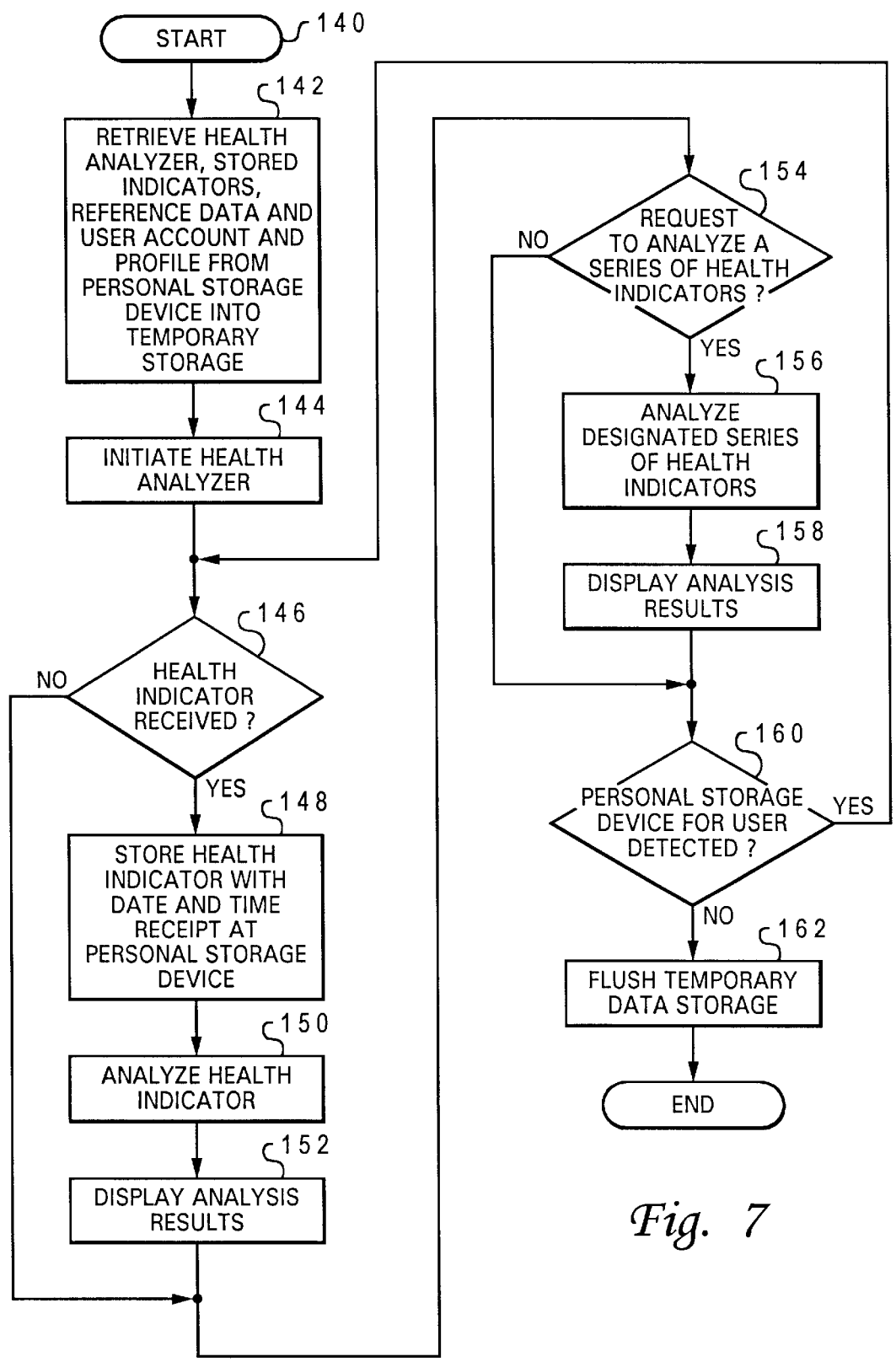
FIG. 7 depicts a high level logic flowchart of a process and program for processing health indicators received at a personal health monitor in accordance with the method, system and program of the present invention.

Referring now to FIG. 7, there is depicted a high level logic flowchart of a process and program for processing health indicators received at a personal health monitor in accordance with the method, system and program of the present invention. As illustrated, the process starts at block 140 and thereafter proceeds to block 142. Block 142 depicts retrieving the health profile, stored indicators, health indicators reference and health analyzer application from personal storage device into temporary storage. Next, block 144 depicts initiating the health analyzer application. The health 30 analyzer application controls the steps depicted in blocks 146–158. In the present embodiment, a copy of the health analyzer application stored in temporary storage is executed on a computer system, however in alternate embodiments, the steps depicted in block 146–158 may be controlled from the health analyzer application executing from the personal storage device where the computer system is a dumb terminal, as previously described. Block 146 illustrates a determination as to whether or not a health indicator is received. If a health indicator is not received, the process passes to block 154. If a health indicator is received, the process passes to block 148. Block 148 depicts storing the health indicator with data and time receipt in the health indicator storage of the personal storage device. Thereafter, block 150 illustrates analyzing the health indicator utilizing the health indicator reference and health profile. Next, block 152 depicts displaying the results from the analysis and the process passes to block 154. In particular, the analysis is preferably displayed according to any output preferences in the user's health profile. In addition, in displaying the results, indicators of whether or not the received physical health indicators are within an acceptable range of physical health levels for the user are provided. Moreover, in addition to displaying analysis, control signals may be output to health control devices in order to control the devices.

Block 154 depicts a determination as to whether or not a request to analyze a series of health indicators is received. A series of health indicators may include health indicators received over a particular period of time, from a particular type of measurement or other types of filters. If there is not a request to analyze a series of health indicators, the process passes to block 160. If there is a request to analyze a series of health indicators, the process passes to block 156. Block 156 illustrates analyzing the designated series of health indicators utilizing the health indicator reference and health profile. Thereafter, block 158 depicts displaying the results from the analysis and the process passes to block 160.

Block 160 illustrates a determination as to whether or not the personal storage device for the user is still detected. If the personal storage device for the user is still detected, the process passes to block 146. If the personal storage device for the user is not still detected, then the process passes to block 162. Block 162 depicts flushing the temporary data storage of all data associated with the user of the now removed personal storage device and the process ends.

Figure 8:
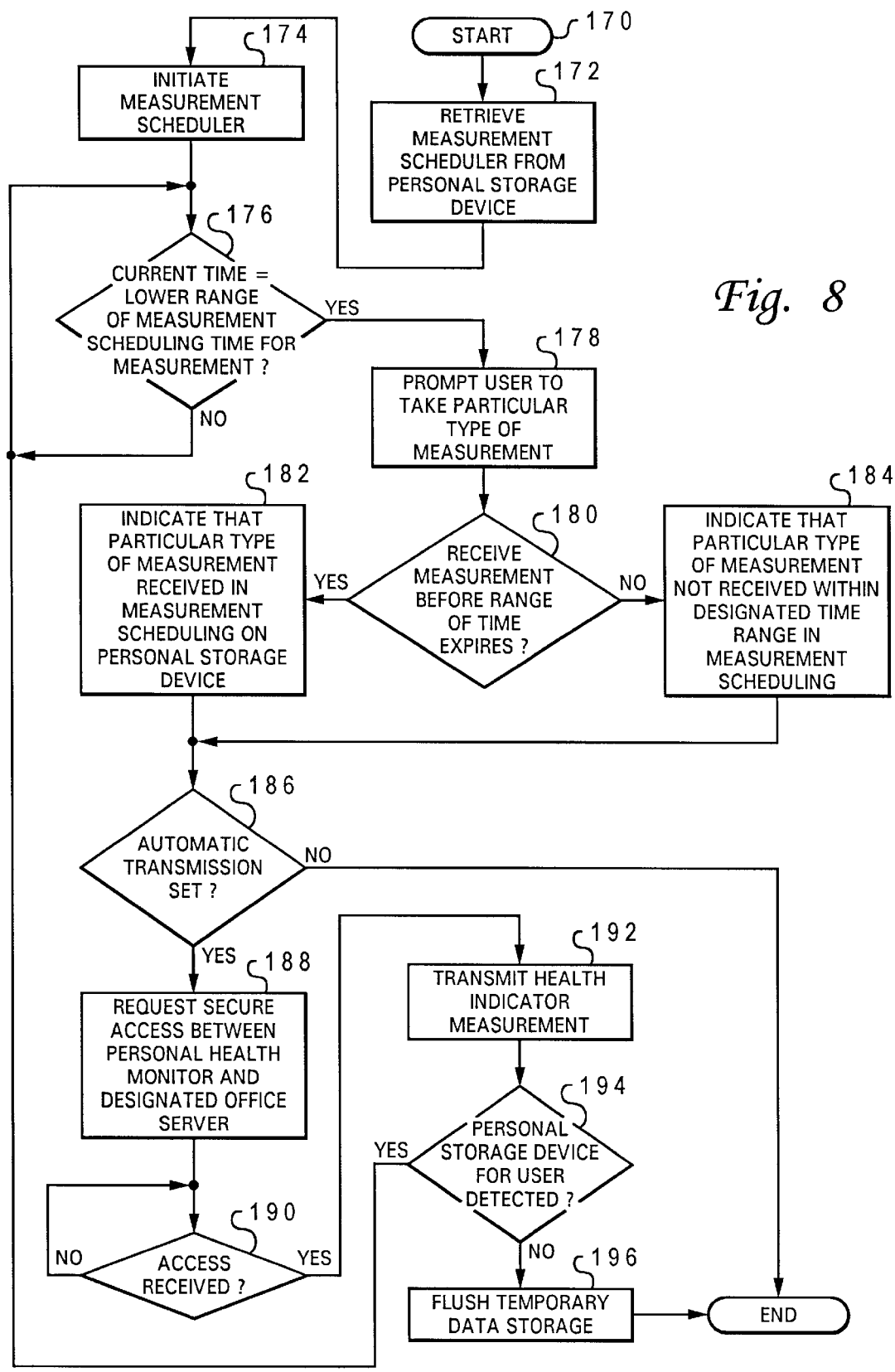
FIG. 8 illustrates a high level logic flowchart of a process and program for monitoring receipt of health indicators in accordance with the method, system and program of the present invention.

With reference now to FIG. 8, there is illustrated a high level logic flowchart of a process and program for monitoring receipt of health indicators in accordance with the method, system and program of the present invention. As depicted, the process start at block 170 and thereafter proceeds to block 172. Block 172 illustrates retrieving the measurement scheduler application from the personal storage device. Thereafter, block 174 depicts initiating the measurement scheduler application.

The measurement scheduler application controls the steps depicted in blocks 176–192. In the present embodiment, a copy of the measurement scheduler application is stored in temporary storage is executed on a computer system, however in alternate embodiments, the steps depicted in blocks 176–192 may be controlled from the measurement scheduler application executing from the personal storage device where the computer system is a dumb terminal, as previously described. Thereafter, block 176 illustrates a determination as to whether or not the current time is equal to the lower range of a measurement scheduling time. If the current time is not equal to the lower range of a measurement scheduling time, the process iterates at block 176. If the current time is equal to the lower range of a measurement scheduling time, the process passes to block 178. Block 178 depicts prompting the user to take a particular type of measurement according to the measurement type scheduled for the measurement scheduling time and the process passes to block 180.

Block 180 illustrates a determination as to whether or not the health indicator measurement is received before the range of time scheduled for the measurement expires. If the measurement is received before the range of time expires, the process passes to block 182. Block 182 depicts indicating that the particular type of measurement is received in the measurement scheduling record and the process passes to block 186. If the measurement is not received before the range of time scheduled for the measurement expires, the process passes to block 184. Block 184 illustrates indicating that the particular type of measurement was not received within the designated range of time in the measurement scheduling record and the process passes to block 186.

Block 186 depicts a determination as to whether or not an automatic transmission for the measurement is set. If an automatic transmission is not set, then the process passes to block 194. If an automatic transmission set, then the process passes to block 188. Block 188 illustrates requesting secure access between the personal computer system and the designated server. Thereafter, block 190 depicts a determination as to whether or not secure access is received. If secure access is not received, the process preferably iterates at block 190 for a limited time. If a secure access is received, the process preferably passes to block 192. Block 192 illustrates transmitting the health indicator measurement to the designated server and the process passes to block 194.

Block 194 illustrates a determination as to whether or not the personal storage device for the user is still detected. If the personal storage device for the user is still detected, the process passes to block 176. If the personal storage device for the user is not still detected, then the process passes to block 196. Block 196 depicts flushing the temporary data storage of all data associated with the user of the now removed personal storage device and the process ends.

It is important to note that, although the present invention has been described in the context of a fully functional computer system, those skilled in the art will appreciate that the mechanisms of the present invention are capable of being distributed as a program product in a variety of forms, and that the present invention applies equally regardless of the particular type of signal-bearing media utilized to actually carry out the distribution. Examples of signal-bearing media include, but are not limited to, recordable-type media such as floppy disks or CD-ROMs and transmission-type media such as analogue or digital communications links.

While the invention has been particularly shown and described with reference to a preferred embodiment, it will be understood by those skilled in the art that various changes in form and detail may be made therein without departing from the spirit and scope of the invention.

What is claimed is:

1. A method for monitoring acceptability of the physical health of an individual, said method comprising the steps of:

receiving a plurality of physical health indicators computed for a particular user in a common transmittable data format at a computer system, wherein each of said plurality of physical health indicators is computed by an electronic health measurement device from among a plurality of diverse electronic health measurement devices monitoring physical health of said particular user;

retrieving acceptable health levels for said particular user from said personal storage device that indicate a normal range of physical health for said particular user as determined from a series of physical health indicators stored at a personal storage device over a particular period of time;

analyzing each of said plurality of physical health indicators at said computer system in view of determined acceptable health levels retrieved at said computer system from said a personal storage device proffered by said particular user; and controlling output of an indicator of acceptability of said plurality of physical health indicators for said particular user from said computer system, in response to said analysis of each of said plurality of physical health indicators, such that a computer system monitors the physical health of an individual in view of acceptable health levels retrieved from said personal storage device.

2. The method for monitoring acceptability of the physical health of an individual according to claim 1, said method further comprising the step of:

retrieving acceptable health levels for said particular user from said personal storage device that indicate a normal range of physical health for said particular user as determined from a health indicator database stored on said personal storage device.

3. The method for monitoring acceptability of the physical health of an individual according to claim 1, said method further comprising the step of:

retrieving acceptable health levels for said particular user from said personal storage device via a personal storage device adapter coupled to said computer system.

4. The method for monitoring acceptability of the physical health of an individual according to claim 1, said method further comprising the step of:

storing said plurality of physical indicators on said personal storage device.

5. The method for monitoring acceptability of the physical health of an individual according to claim 1, said method further comprising the step of:

controlling transmission of a plurality of control signals to a plurality of health control devices that control said physical health of said particular user, in response to said analysis of said plurality of physical health indicators.

6. The method for monitoring acceptability of the physical health of an individual according to claim 1, said method further comprising the step of:

debiting an account for said particular user retrieved from said personal storage device according to usage of said plurality of diverse electronic health measurement devices.

7. A system for monitoring acceptability of the physical health of an individual, said system comprising:

means for receiving a plurality of physical health indicators computed for a particular user in a common transmittable data format at a computer system, wherein each of said plurality of physical health indicators is computed by an electronic health measurement device from among a plurality of diverse electronic health measurement devices monitoring physical health of said particular user;

means for retrieving acceptable health levels for said particular user from said personal storage device that indicate a normal range of physical health for said particular user as determined from a series of physical health indicators stored at a personal storage device over a particular period of time;

means for analyzing each of said plurality of physical health indicators at said computer system in view of determined acceptable health levels retrieved at said computer system from said personal storage device proffered by said particular user; and means for controlling output of an indicator of acceptability of said plurality of physical health indicators for said particular user from said computer system, in response to said analysis of each of said plurality of physical health indicators, such that a computer system monitors the physical health of an individual in view of acceptable health levels retrieved from said personal storage device.

8. The system for monitoring acceptability of the physical health of an individual according to claim 7, said system further comprising:

means for retrieving acceptable health levels for said particular user from said personal storage device that indicate a normal range of physical health for said particular user as determined from a health indicator database stored on said personal storage device.

9. The system for monitoring acceptability of the physical health of an individual according to claim 7, said system further comprising:

means for retrieving acceptable health levels for said particular user from said personal storage device via a personal storage device adapter coupled to said computer system.

10. The system for monitoring acceptability of the physical health of an individual according to claim 7, said system further comprising:

means for storing said plurality of physical indicators on said personal storage device.

11. The system for monitoring acceptability of the physical health of an individual according to claim 7, said system further comprising:

means for controlling transmission of a plurality of control signals to a plurality of health control devices that control said physical health of said particular user, in response to said analysis of said plurality of physical health indicators.

12. The system for monitoring acceptability of the physical health of an individual according to claim 7, said system further comprising:

means for debiting an account for said particular user retrieved from said personal storage device according to usage of said plurality of diverse electronic health measurement devices.

13. A program for monitoring acceptability of the physical health of an individual, residing on a computer usable medium having computer readable program code means, said program comprising:

means for enabling reception of a plurality of physical health indicators computed for a particular user in a common transmittable data format at a computer system, wherein each of said plurality of physical health indicators is computed by an electronic health measurement device from among a plurality of diverse electronic health measurement devices monitoring physical health of said particular user;

means for enabling retrieval of acceptable health levels for said particular user from said personal storage device that indicate a normal range of physical health for said particular user as determined from a series of physical health indicators stored at a personal storage device over a particular period of time;

means for analyzing each of said plurality of physical health indicators at said computer system in view of determined acceptable health levels retrieved at said computer system from said personal storage device proffered by said particular user; and means for controlling output of an indicator of acceptability of said plurality of physical health indicators for said particular user from said computer system, in response to said analysis of each of said plurality of physical health indicators, such that a computer system monitors the physical health of an individual in view of acceptable health levels retrieved from said personal storage device.

14. The program for monitoring acceptability of the physical health of an individual according to claim 13, said program further comprising:

means for storing said plurality of physical indicators on said personal storage device.

15. The program for monitoring acceptability of the physical health of an individual according to claim 13, said program further comprising:

means for debiting an account for said particular user retrieved from said personal storage device according to usage of said plurality of diverse electronic health measurement devices.

16. A method for controlling the physical health of an individual, said method comprising the steps of:

receiving a plurality of physical health indicators computed for a particular user in a common transmittable data format at a computer system, wherein each of said plurality of physical health indicators is computed by an electronic health measurement device from among a plurality of diverse electronic health measurement devices monitoring said particular user;

retrieving acceptable health levels for said particular user from said personal storage device that indicate a normal range of physical health for said particular user as determined from a series of physical health indicators stored at a personal storage device over a particular period of time;

analyzing each of said plurality of physical health indicators at said computer system in view of determined acceptable health levels retrieved at said computer system from said personal storage device proffered by said particular user; and controlling output of a plurality of control signals to a plurality of health control devices that each control a particular parameter of said physical health of said particular user, in response to said analysis of each of said plurality of physical health indicators, such that a computer system controls the physical health of an individual in view of acceptable health levels for said individuals retrieved from said personal storage device.

17. A system for controlling the physical health of an individual, said system comprising:

means for receiving a plurality of physical health indicators computed for a particular user in a common transmittable data format at a computer system, wherein each of said plurality of physical health indicators is computed by an electronic health measurement device from among a plurality of diverse electronic health measurement devices monitoring said particular user;

means for retrieving acceptable health levels for said particular user from said personal storage device that indicate a normal range of physical health for said particular user as determined from a series of physical health indicators stored at a personal storage device over a particular period of time;

means for analyzing each of said plurality of physical health indicators at said computer system in view of determined acceptable health levels retrieved at said computer system from said personal storage device proffered by said particular user; and means for controlling output of a plurality of control signals to a plurality of health control devices that each control a particular parameter of said physical health of said particular user, in response to said analysis of each of said plurality of physical health indicators, such that a computer system controls the physical health of an individual in view of acceptable health levels for said individuals retrieved from said personal storage device.

18. A program for controlling the physical health of an individual, residing on a computer readable medium having computer readable program code means, said program comprising:

means for enabling reception of a plurality of physical health indicators computed for a particular user in a common transmittable data format at a computer system, wherein each of said plurality of physical health indicators is computed by an electronic health measurement device from among a plurality of diverse electronic health measurement devices monitoring said particular user;

means for retrieving acceptable health levels for said particular user from said personal storage device that indicate a normal range of physical health for said particular user as determined from a series of physical health indicators stored at a personal storage device over a particular period of time;

means for analyzing each of said plurality of physical health indicators at said computer system in view of determined acceptable health levels retrieved at said computer system from said personal storage device proffered by said particular user; and means for controlling output of a plurality of control signals to a plurality of health control devices that each control a particular parameter of said physical health of said particular user, in response to said analysis of each of said plurality of physical health indicators, such that a computer system controls the physical health of an individual in view of acceptable health levels for said individuals retrieved from said personal storage device.

19. A data storage medium comprising:

a plurality of acceptable health indicator levels stored for a particular user; and an interface for enabling access to stored data, wherein said interface enables access to said plurality of acceptable health indicators by a controller for a plurality of health control systems that each respectively affect one of a plurality of parameters of the physical health of said particular user.

20. The data storage medium according to claim 19, wherein data is accessed via said interface by a personal storage device adapter coupled to a data processing system.

21. The data storage medium according to claim 19, further comprising a smart card storing a plurality of acceptable health indicator levels stored for a particular user.

22. The data storage medium according to claim 19, wherein said data storage medium further comprises a database of physical health indicators measured for said particular user.

23. The data storage medium according to claim 19, wherein said interface enables reception of a current physical health indicator for said particular user from a computer system with access to a health measurement device that detects one of a plurality of parameter of the physical health of said particular user.

24. The data storage medium according to claim 19, wherein said data storage medium further comprises a wherein analyzer application that when executed on a computer system analyzes a plurality of physical health indicators in view of said plurality of acceptable health indicator levels.

25. The data storage medium according to claim 19, wherein said data storage medium further comprises an account that for said particular user that is debitable.

26. The data storage medium according to claim 19, wherein said date storage medium further comprises an electronic schedule of designated times for taking measuring a particular physical health indicator for said particular user.

* * * * *

UNITED STATES PATENT AND TRADEMARK OFFICE
CERTIFICATE OF CORRECTION

PATENT NO.    : 6,440,068 B1
DATED         : August 27, 2002
INVENTOR(S)   : Brown et al.

It is certified that error appears in the above-identified patent and that said Letters Patent is hereby corrected as shown below:

<u>Title page, Item [54] and Column 1, line 1,</u>
Please replace the first word in the title: "MEASURING" with -- MANAGING --.

<u>Column 3,</u>
Line 56, please delete "id" between the words "devices" and "for".

<u>Column 18,</u>
Line 67, please replace "wherein" with -- health --.

Signed and Sealed this

Eighth Day of July, 2003

JAMES E. ROGAN
*Director of the United States Patent and Trademark Office*